United States Patent
Bullen et al.

(10) Patent No.: US 7,241,565 B2
(45) Date of Patent: Jul. 10, 2007

(54) LIQUID INTERFACE CONFIGURATIONS FOR AUTOMATED PATCH CLAMP RECORDING

(75) Inventors: Andrew Bullen, Wallingford, CT (US); Charles David Weaver, Wallingford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 548 days.

(21) Appl. No.: 10/305,828

(22) Filed: Nov. 27, 2002

(65) Prior Publication Data

US 2003/0138767 A1   Jul. 24, 2003

Related U.S. Application Data

(60) Provisional application No. 60/338,715, filed on Nov. 30, 2001.

(51) Int. Cl.
*C12Q 1/00* (2006.01)

(52) U.S. Cl. .............................................. 435/4; 435/6

(58) Field of Classification Search ..................... None
See application file for complete search history.

(56) References Cited

U.S. PATENT DOCUMENTS 6,063,260 A   5/2000   Olesen et al.

FOREIGN PATENT DOCUMENTS

| WO | WO 98/50791 | 11/1998 |
| WO | WO 99/66329 | 12/1999 |
| WO | WO 00/34776 | * 6/2000 |
| WO | WO 00/71742 | 11/2000 |
| WO | WO 01/71349 | 9/2001 |

OTHER PUBLICATIONS

Tie et al., British Journal of Pharmacology 130:1967-1975 (2000).*
Snyder et al., Pflugers Archiv-European Journal of Physiology, (Aug. 1999) vol. 438, No. 3, pp. 405-411.*
Varming, Neuropharmacology 38:1875-1881 (1999).*
Egee et al., Journal of Physiology 504(1):57-63 (1997).*

* cited by examiner

*Primary Examiner*—Mark L. Shibuya
*Assistant Examiner*—Jeffrey S Lundgren
(74) *Attorney, Agent, or Firm*—Paul D. Golian (57) ABSTRACT

A method of automatically conducting patch clamp testing is provided wherein a liquid interface is utilized. The liquid interface is defined in a liquid suspension between layers of distinct densities such that cells introduced into the liquid suspension float towards the interface. Thus, the cells are locatable relative to the interface.

20 Claims, 6 Drawing Sheets

LIQUID INTERFACE CONFIGURATIONS FOR AUTOMATED PATCH CLAMP RECORDING

CROSS-REFERENCE TO RELATED APPLICATION

This application claims priority to U.S. Provisional Patent Application No. 60/338,715, filed Nov. 30, 2001.

FIELD OF THE INVENTION

The present invention relates generally to techniques for repeatedly positioning an instrument relative to one or more cells for testing and, more particularly, to an automated technique for positioning a pipette or an array of pipettes for measuring cellular electrical properties including ion channel currents, membrane potential, transporter flux and cell capacitance.

DESCRIPTION OF THE PRIOR ART

Ion channel measurement plays an important role in determining the effect of compounds and the like at the cellular level. Ion channels are transmembrane proteins that form pores in a cell membrane, which, in turn, allow ions to pass from one side of the cell membrane to another. The activity of these channels influences cell membrane potential and are responsible for mediating changes in overall cell excitability.

Patch clamp techniques are commonly used for performing ion channel measurements. Certain patch clamp techniques are described in Sakmann and Neher, "Single-Channel Recording," Plenum, 1995. Typically, such techniques involve the use of a glass pipette or micropipette to contact with, and ideally attach to, a cell. A micropipette is a hollow glass tube having a polished blunt tip and an aperture therethrough. Methodologies for forming micropipettes are disclosed in Brown and Flaming, "Advanced Micropipette Techniques for Cell Physiology", 1989, and a cross-section of a blunt tip of a prior art micropipette is displayed in FIG. 1.

To have the micropipette contact with, and attach to, the cell, standard cell location and pipette placement techniques may be used. Alternatively, the cell may be positioned, for example, at the aperture of the micropipette by manipulating an electric field via an electrode positioned in proximity to the aperture. A critical step in any patch clamp recording process is the formation of an acceptable seal between the outside surface of the blunt tip of the micropipette and the attached cell. An acceptable seal is often referred to as a "giga-ohm seal" because it generally demonstrates electrical resistance measurable in giga-ohms. (Reference herein to forming a "seal" shall mean the formation of an electrically acceptable seal having sufficient electrical resistance to be measurable; it is preferred that the electrical resistance be greater than or equal to 1 giga-ohm, but may be less than.) Conventional techniques are known for forming a seal.

After seal formation, it is often desired to obtain "whole cell" access which is achieved via electroporation, additional suction, chemopermeabilization, or a combination thereof. (Mere attachment of the micropipette, even in a sealed state, to the cell provides limited "on cell" configuration which can be used to measure individual ion channel properties from the small patch of membrane under the electrode.) Sakmann & Neher. Test compounds and the like may then be applied to the cell, and changes in its electrical properties (i.e., current, potential, conductance and capacitance) may thereafter be measured. These measurements, in turn, can be used to assay ion channel activity, transporter activity, or changes in the properties of cell membrane caused by cell-to-cell interactions, cell-to-cell fusion, viral infection, endocytosis, exocytosis, membrane cycling and membrane-to-ligand interactions.

Various patch clamp techniques employing blunt tip micropipettes are disclosed in U.S. Pat. No. 6,063,260 and PCT Publication Nos. WO 98/50791, WO 99/66329 and WO 00/34776.

Figure 1:
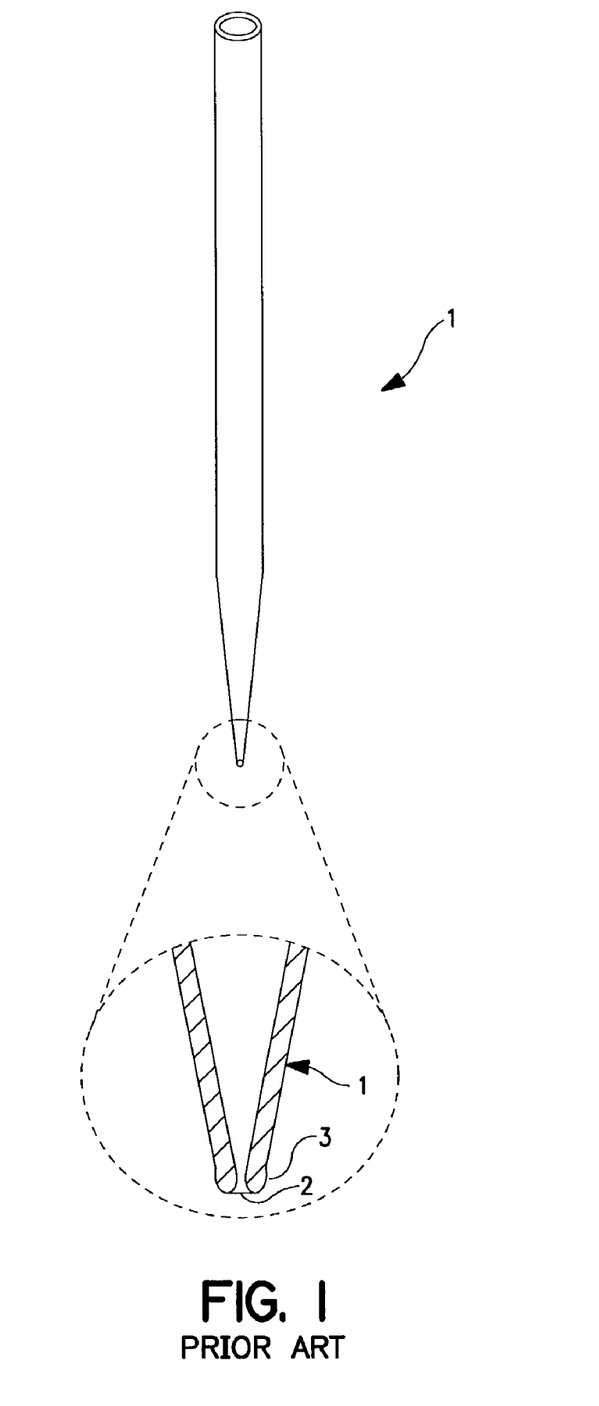
FIG. 1 is a schematic of a prior art pipette.

FIG. 1 displays a cross-section of a blunt tip pipette 1 as found in conventional technologies. The pipette 1 typically has an aperture 2 disposed at the tip 3 thereof. Such pipettes are typically composed of glass. To perform patch clamping, the tip 3 is positioned to contact a subject cell. In the prior art, the act of positioning the micropipette tip is tedious, requiring initial cell location (e.g., on a dish; in a cell bath); and, positioning the micropipette properly relative to the located cell. With prior art techniques, the processes of cell location and micropipette positioning are manually achieved, typically using a high quality microscope, and a high quality three axis micromanipulator (with sub-micron resolution in each axis) to control location of the micropipette tip. As is readily appreciated, the skill of the operator determines the speed and efficiency by which patch clamping can be conducted. Thus, a high degree of skill is required to perform patch clamp techniques using existing technologies. Accordingly, there is a need for a new technique which readily addresses certain problems of the prior art.

Techniques have been developed to facilitate cell contacting, such as with introducing a slight electrical field at the tip of the micropipette. In addition, a technique has been developed which, through automation, allows for repeated cell location and proper micropipette positioning, such as a technique disclosed in WIPO International PCT Publication No. WO 00/34776. This technique relies on a liquid medium or a liquid/air interface defined at the tip of an inverted pipette. Cells are suspended at the interface, or near the surface of the liquid medium, due to surface tension and locatable thereat. The cells are then accessible to a microstructure electrode. Upon cell contacting, seal formation is achieved using known techniques, and electrophysiological properties of the cell are measured by the electrode. Several deficiencies, however, are found with this technique. First, debris collects at the interface and interferes with, and even spoils, the ability to have seal formation. Second, the meniscus at the interface creates difficulties in developing seal formation.

A technique has been developed in the prior art referred to as a "blind" patch clamp method, wherein recordings are made from individual cells by randomly plunging a pipette into bodily tissue. This method has been used with whole cell recording of neurons in slices of reptilian and mammalian cerebral cortex. In these tissues, cells are abundant and tightly packed.

SUMMARY OF THE INVENTION

With the subject invention, a method is provided for automating the patch clamp technique for testing electrophysiological properties of cells, including cellular resistance, capacitance, transmembrane potential, and conductance. The technique may be used to evaluate cellular features which affect the aforementioned electrophysiological characteristics, such as ion channels and electrogenic transporters. The subject invention enables cells to be accurately and repeatedly positioned relative to the tip of a micropipette so as to allow the tip to contact one of the cells. The method further facilitates the attachment of the cell to the pipette and generation of an acceptable seal therewith and is usable with both whole cell and on cell configurations. (As used herein, and generally understood in the art, the term "whole cell" refers to a testing configuration where an aperture formed in a pipette is in communication with a hole that extends through the lipid bi-layer (i.e., membrane) of a cell such that electrophysiological data obtained during testing result from the cell's entire plasma membrane, and its constituent ion channels and/or electrogenic transporters, thus, the "whole" cell. As used herein, and generally understood in the art, the term "on cell" refers to a testing configuration where an aperture formed in a pipette does not communicate with the interior of a cell (i.e., the pipette contacts partially or wholly intact membrane).)

In one aspect of the invention, a liquid suspension of at least first and second layers is utilized, wherein the layers have distinct densities so as to define an interface therebetween. With the liquid suspension, a layer of cells may be located at, or in proximity to, the interface between the layers. In this manner, a cell population may be dispersed in a known plane.

In a second aspect of the invention, it is desired to position the tip of a micropipette in, or in proximity to, the layer of suspended cells. Although the tip of the micropipette can be positioned using a visual observation, it is preferred to use automated techniques. For example, in one desirable method, the offset potential (also referred to as "junction potential") between the recording pipette and a reference electrode is monitored. The offset potential is different between solutions of different ionic compositions (or can be artificially manipulated to be different). By monitoring the offset potential, the interface of the liquid suspension can be located without manual intervention. Preferably, the reference electrode (also referred to as the ground electrode) is in close proximity to a recording electrode located in the pipette. In this manner, the two electrodes are located generally in the same plane and changes in offset potential therebetween may accurately position the tip of the pipette relative to the interface of the liquid suspension. A particularly desirable location for the reference electrode is within a guard pipette. Alternatively, the reference electrode is disposed in one of the layers of the liquid suspension away from the micropipette. A measurable electrical potential difference is generated between the reference and recording electrodes with the electrodes being in different layers of the suspension. Accordingly, a change in electrical potential, as measured between the two electrodes, indicates the positioning of the tip of the micropipette relative to the liquid interface. In one configuration, with the reference electrode being located above the interface, an electrical potential is generated with the tip of the micropipette breaching the interface. Conversely, with the reference electrode being located below the interface, an electrical potential is initially generated, which is affected by the tip of the micropipette breaching the interface.

Other techniques for locating the tip of the micropipette relative to the interface include visual monitoring and monitoring the resistance of the pipette (which changes upon reaching the interface and contacting cell(s)). Also, visual monitoring can be automated using any technique known to those skilled in the art.

In addition, the cells can be positioned relative to the interface (positioned about the interface and/or moved relative to the interface) using any technique known to those skilled in the art, such as laser tweezers.

In practicing the method of the subject invention, a first layer of the liquid suspension is prepared, having a density range generally greater than the density of cells to be tested. A population of cells is mixed into the first layer, and a second, less-dense liquid (having a density range generally less than that of the cells) is disposed upon the mixture. The liquids are allowed to settle so as to generally form a stratified liquid suspension having an interface defined therein. A density modifying agent can form a component of the liquid forming the first layer. The density of the cells cause them to float into or in proximity to the interface. A micropipette is introduced, with the tip being positioned in, or in proximity to, the interface such that it may contact a cell. During introduction of the micropipette, it is preferred that a slight positive pressure be applied inside of the micropipette so that a cell does not contact the micropipette until it is properly positioned. Once the tip of the micropipette is properly positioned relative to the interface, positive pressure within the micropipette is replaced with negative pressure and electrical resistance of the micropipette is monitored in a voltage clamping manner known in the prior art. Upon a cell contacting the micropipette, attachment to the tip is facilitated by applying negative pressure internally to the micropipette. If an acceptable seal is not spontaneously generated, an electrical potential is generated so as to improve the attachment of the cell and improve the seal quality. Once the seal is generated, and the whole cell configuration achieved, the clamped cell may be used in compound screening assays to determine effects on ion channels, electrogenic transporters, and other activities that affect cellular electrical properties of the compounds.

With the subject invention, the need to image cells during seal formation is eliminated, and, thus, can be conducted without a microscope, skilled operator or micromanipulators. Furthermore, the invention is compatible with known automation methods. Moreover, the invention allows for use of cells in solutions, which significantly simplifies traditional culture and plating procedures.

These and other features of the invention will be better understood through a study of the following detailed description and accompanying drawings.

DETAILED DESCRIPTION OF THE INVENTION

Referring to the Figures, a method is provided for automating the patch clamp technique for testing electrophysiological properties of cells, including cellular resistance, capacitance, transmembrane potential, and conductance. In addition, this method may be used to evaluate cellular features, such as ion channels and electrogenic transporters.

Figure 2:
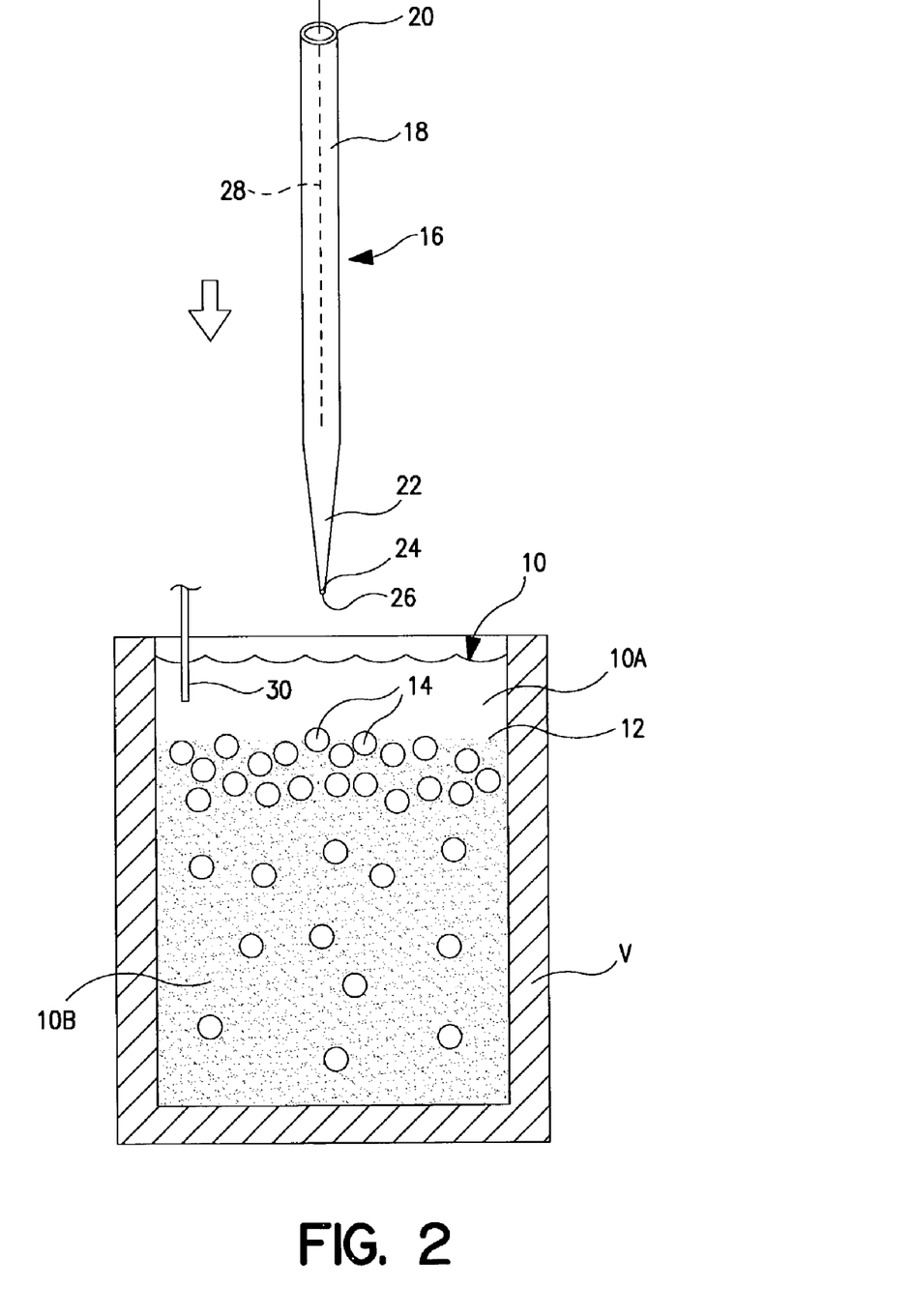
FIG. 2 is a schematic of a patch clamp technique in accordance with the subject invention.

With reference to FIG. 2, a liquid suspension 10 of at least first and second layers 10A and 10B is shown with an interface 12 being defined therebetween. The liquid suspension 10 may be accommodated in any vessel V known to those skilled in the art, such as a well of a multiwell plate. The densities of the first and second layers 10A and 10B are desirably distinct such that the layers are generally stratified with the interface 12 being defined therebetween. The densities may be generally fixed throughout each layer or lie within a range of densities for each layer (e.g., gradiently disposed), although it is preferred that the densities of the layers 10A and 10B be distinct and different with no overlap. It is also preferred that the ionic compositions of the first and second layers 10A and 10B be sufficiently distinct such that an offset potential may be generated between the layers 10A, 10B.

A plurality of cells 14 are suspended in the liquid suspension 10. It is preferred that the density of the cells 14 be generally less than the density of the second (lower) layer 10B, and generally greater than the density of the first (upper) layer 10A. By way of non-limiting example, the more dense second layer 10B may have a density in the range of 1.10 to 1.3 g/ml; the less dense first layer 10A may have a density in the range of 1.01 to 1.10 g/ml; with the cells 14 having a density in the range of 1.04 to 1.13 g/ml. (As used herein, a "more dense" liquid or suspension shall refer to a liquid or suspension having a density or range of densities generally greater than (may have some overlap with) the range of densities of the cells (i.e., 1.04 to 1.13 g/ml). A "less dense" liquid or suspension shall refer to a liquid or suspension having a density or range of densities generally less than (may have some overlap with) the range of densities of the cells.) Accordingly, due to the differences in density, the cells 14 will tend to locate in, or in proximity to, the interface 12. As such, a locatable plane of the cells 14 may be defined.

Figure 4A:
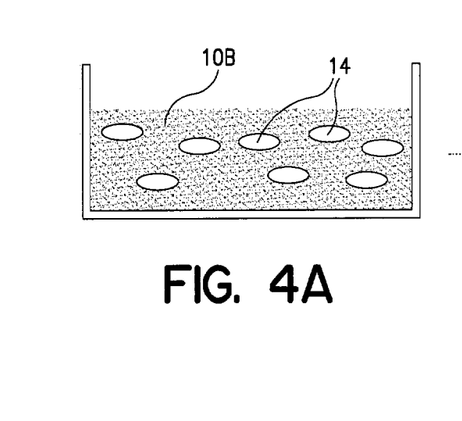
FIGS. 4A–4C depict a method of preparing a liquid suspension for use with the subject invention.
Figure 4B:
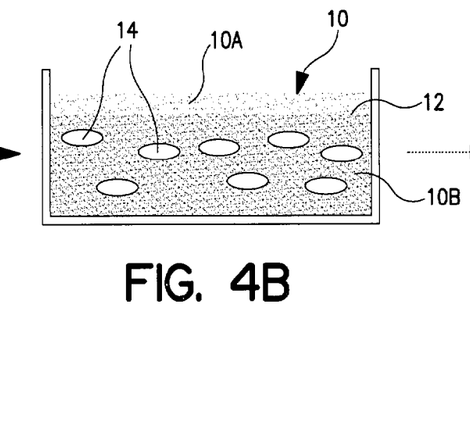
Figure 4C:
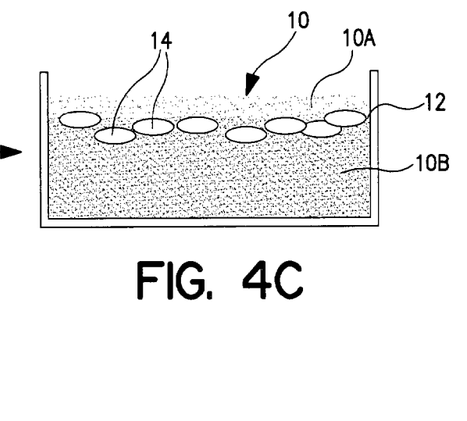

Referring to FIGS. 4A–4C, a method for preparing the liquid suspension 10 with the cells 14 therein is depicted. With reference to FIG. 4A, the cells 14 are mixed into the more dense liquid of the layer 10B. Thereafter, as shown in FIG. 4B, the less dense liquid of the layer 10A is disposed atop the layer 10B. The suspension 10 is allowed to settle, wherein the liquids separate to define the layers 10A and 10B with the interface 12 being therebetween, and the cells 14 float into, or in proximity to, the interface 12. To enhance visual confirmation that the liquid suspension 10 has sufficiently stratified, an optical marker, such as fast green or phenol red, may be disposed in one or both of the layers 10A, 10B. As an alternative, the cells 14 may be initially mixed into the less dense liquid of the layer 10A, with the mixed solution being disposed atop the more dense layer 10B. As a further variation, and the most preferred method, the less dense liquid of the layer 10A is initially disposed into the vessel. Thereafter, the more dense liquid of the layer 10B, with cells being mixed therein, is introduced through a port (not shown) in communication with the less dense liquid of the layer 10A. Preferably, the port is located in the bottom of the vessel. The more dense liquid of the layer 10B may be introduced through a gravity feed or be forcibly injected (e.g., by injection with a syringe) generally below the less dense liquid of the layer 10A.

As an exemplary illustration of the subject invention, density-gradient media, such as tiny silica particles coated with polyvinyl pyrrolidone (PVP) sold under the trademark "PERCOLL" by Amersham Pharmica Biotech, are mixed with an appropriate liquid (e.g., extracellular saline) to create the more dense layer. The less dense layer may be of normal density extracellular saline (normal density=1.011 g/ml) (i.e., without density-gradient media). To maintain cell health in the liquid suspension 10, care must be taken to maintain physiological ionic strength and acidity (pH). Other density gradient media known in the art may be used, and may be substituted for the "PERCOLL" particles described above, such as that sold under the trademarks "FICOLL", "OPTIPREP", and "NYCODENZ".

Because of the difference in densities, generally healthy ("intact") cells will collect at the interface 12. Cell debris and dead cells (having different densities) will tend to be away from the interface 12, and, thus, not interfere with cell contacting and seal formation with healthy cells.

Although reference has been made herein to the use of two layers 10A, 10B, any number of layers (or a gradient) may be used to define multiple interfaces or a continuous gradient. Additionally, cell populations including cells of different densities may be used in such multi-interface liquid suspensions, where different groups of cells float to and are located relative to different interfaces.

With the liquid suspension 10 having been prepared, testing of the cells 14 may be permitted, such as patch clamp testing, and other techniques. Although the discussion herein will focus on patch clamp testing, it is to be understood that other testing techniques may be utilized.

Figure 3:
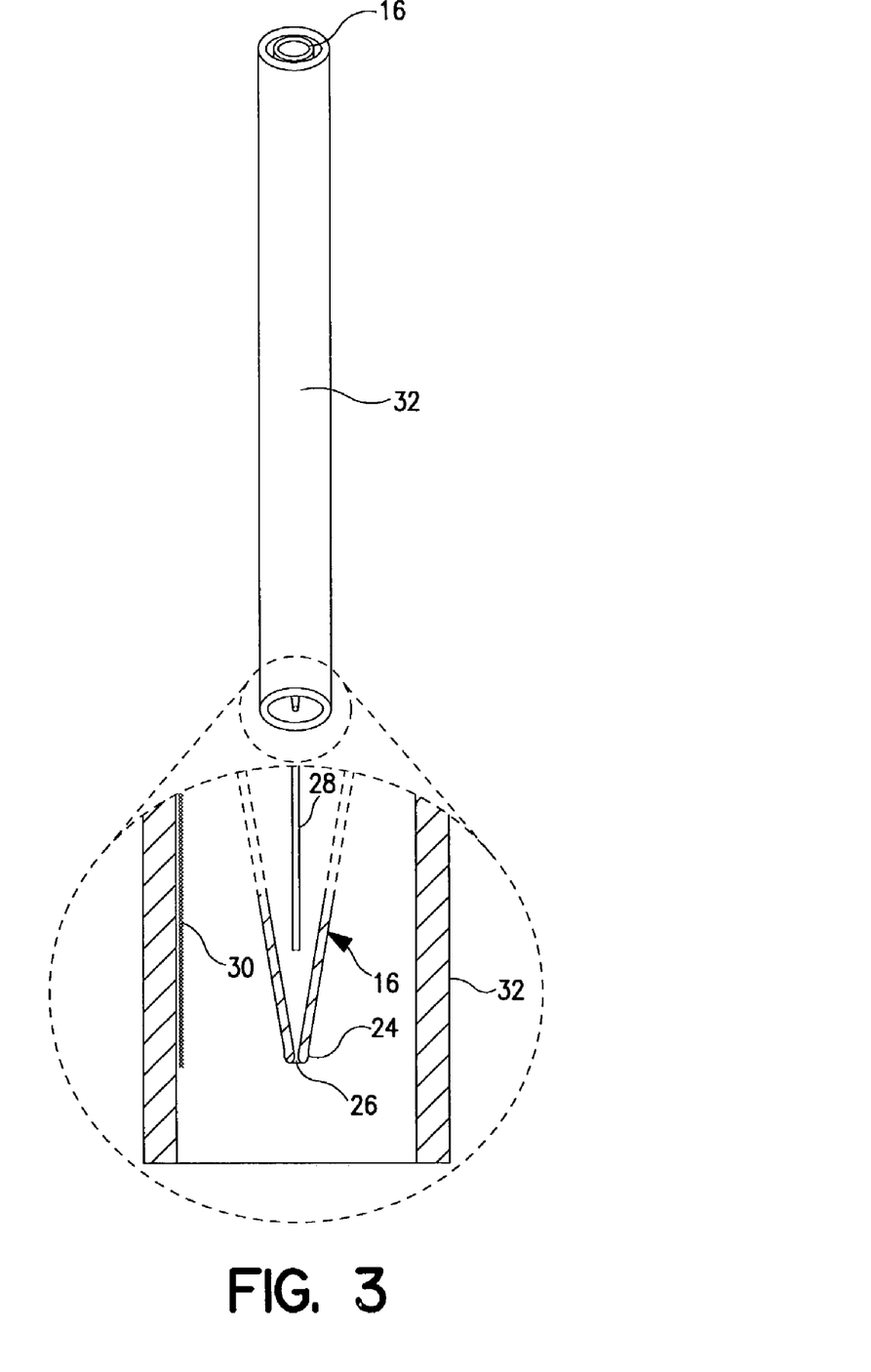
FIG. 3 is a schematic of a pipette having a guard pipette thereabout with a reference electrode.

Referring again to FIG. 2, a pipette 16 is introduced to perform patch clamping of one of the cells 14. (The terms "pipette" and "micropipette" are used interchangeably herein.) The pipette 16 may be of any type known to those skilled in the art, including conventional pipette designs as well as a unique enlarged-tip ("bubble") pipette disclosed in copending U.S. Patent Application No. 60/338,538 (BMS Reference No. D0130PSP) to the inventors and assignee herein. By way of exemplary representation, the pipette 16 includes a tubular body 18 having a distal end 20 and a tapered proximal end 22 which terminates in a tip 24. An aperture 26 extends through the tip 24 into communication with the lumen of the tubular body 18. To facilitate patch clamp testing, and the measuring of electrical properties during seal formation, a recording electrode 28 is disposed to extend into, or in proximity to, the aperture 26. Additionally, as shown in FIG. 3, a guard pipette 32 may be disposed about the pipette 16 so as to cover the tip 24.

Advantageously, the method of the subject invention may rely on automation to properly locate the tip 24 of the pipette 16 relative to the interface 12. By positioning the tip 24 in, or in proximity to, the interface 12, the tip 24 may contact one of the cells 14. It must be noted that the interface 12 is not necessarily a clearly defined layer with the cells 14 being suspended therein. Rather, some of the cells 14 may be located in the layers 10A, 10B. By increasing the number of cells 14 in the cell population, the likelihood of the tip 24 coming into contact with one of the cells 14 is increased. However, inadvertent contact with multiple cells by the pipette 16 should be avoided to ensure that testing integrity of the pipette 16 is maintained. Thus, the cell population should not be excessive.

In a preferred automated method to position the tip 24 of the pipette 16, a reference electrode 30 is utilized to measure offset potential relative to the recording electrode 28. Preferably, as shown in FIG. 3, the reference electrode 30 is disposed in the guard pipette 32 so as to be in proximity to the tip 24, and thus, the recording electrode 28. Additionally, the reference electrode 30 and the recording electrode 28 may be disposed generally at the same elevation relative to the pipette 16, thus, being generally coplanar. Alternatively, the electrodes 28, 30 may be offset, with, for example, the reference electrode 30 extending beyond the recording electrode 28. With this arrangement, the interface 12 may be located without the tip 24 engaging the interface 12.

Offset potential measurement between the two electrodes, 28, 30 will indicate accurately the location of the tip 24 relative to the interface 12. The reference electrode 30 may be a silver wire coated with polytetrafluoroethylene having an exposed tip which has been chloride coated (to generate a silver/silver-chloride electrode). The detection of changes in offset potential will indicate the exposure of different ionic solutions to the electrodes 28 and 30. Thus, the interface 12 can be accurately located by pre-determining the offset potential change relative to the interface (or a change of offset potential from leaving the less dense layer 10A). The pre-determination can be achieved by repeated testing or by utilizing theoretical calculations based on the size, charge and mobility of the ions in the layers 10A, 10B (e.g., a computer program sold under the trade name "JPCalc" by Axon Instruments may be utilized). It is preferred to reduce the amount of counter ions (e.g., by using a di-valent anion) in the liquid suspension 10 to increase the size of the junction potential. The offset potential may be as high as 15 mV.

By way of non-limiting example, disodium asparate may be used to replace sodium chloride and reduce the absolute number of anions in the more dense liquid of the layer 10B to generate the offset potential. With the less dense liquid of the layer 10A being normal density extracellular saline, the more dense liquid of the layer 10B may be formed as follows:

TABLE 1

| Component | Concentration (mM) |
|---|---|
| $Na_2Asp$ (Mole wt. = 250) | 60 |
| NaCl | 20 |
| KCl | 2.5 |
| $CaCl_2$ | 2.5 |
| $MgCl_2$ | 1.0 |
| HEPES, pH 7.3 w/NaOH | 10 |
| Glucose | 5 |

The final density of this solution is approximately 1.10 g/ml with osmolality of 305–310 mOsm.

Alternatively, the reference electrode 30 may be disposed in one of the layers 10A, 10B and away from the pipette 16. Thus, by monitoring offset potential between the reference electrode 30 and the recording electrode 28, the position of the tip 24 relative to the interface 12 may be determined. For example, as shown in FIG. 2, in a preferred arrangement, the reference electrode 30 is disposed in the layer 10A, with either no or a negligible offset potential difference between the recording electrode 28 and the reference electrode 30 being detected (especially after electronic offset correction). However, with the tip 24 of the pipette, and thus the recording electrode 28, coming into contact with the interface 12, a change in electrical potential between the electrodes 28 and 30 will be detected. Likewise, if the reference electrode 30 was to be submerged into the layer 10B, an initial offset potential difference will be detected between the electrodes 28 and 30, which is affected by interaction of the tip 24 and the interface 12. In either regard, the tip 24 can be accurately positioned relative to the interface 12.

Other position techniques may be used, such as visual observation, and monitoring the resistance of the pipette 16 (which changes upon reaching the interface 12 and contacting one of the cells 14). Laser tweezers may also be used to position the cells 14 relative to the interface 12 and/or the pipette 16.

Figure 5:
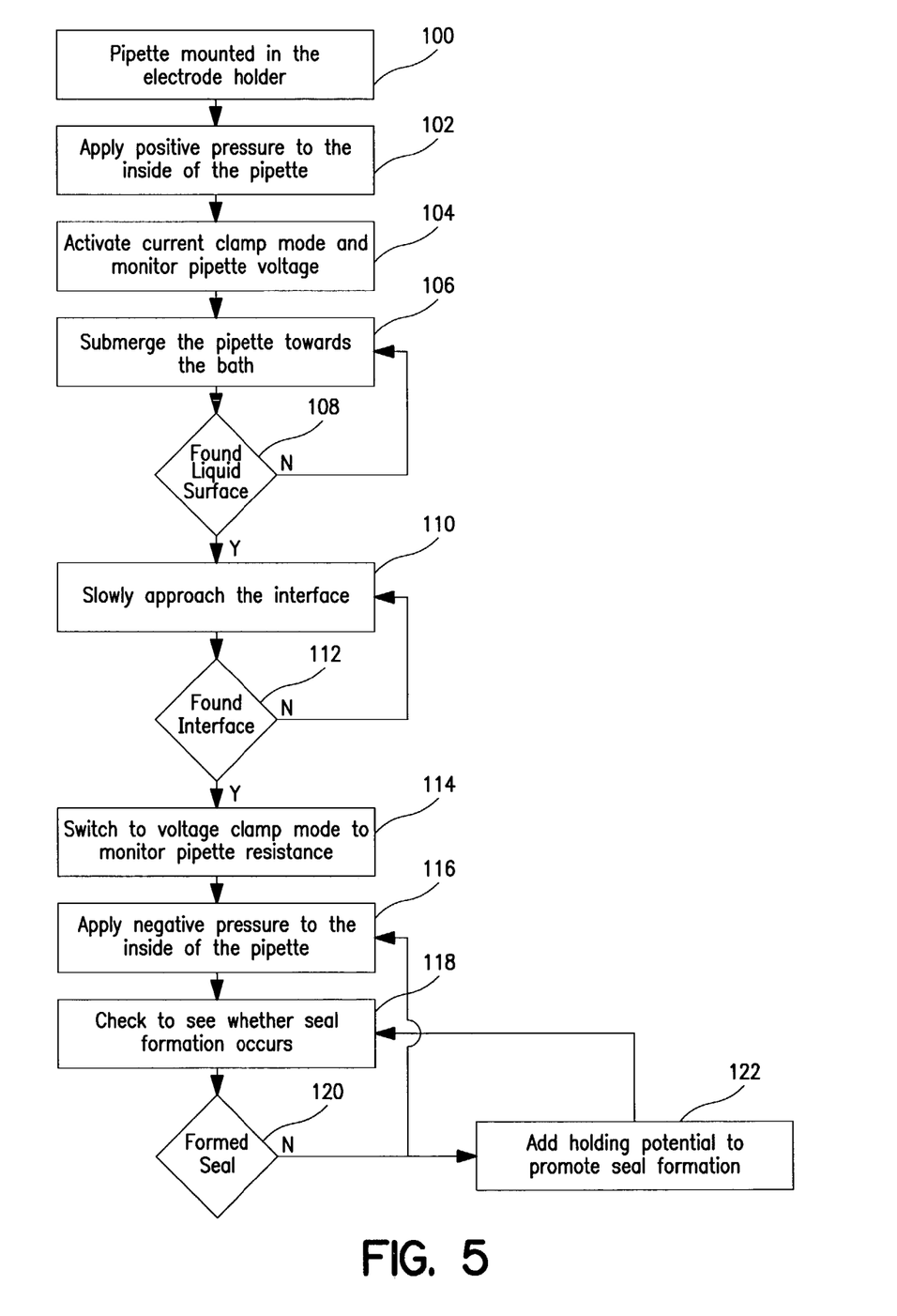
FIG. 5 is a flow chart setting forth an exemplary method of practicing the subject invention; and,
FIG. 6 is a schematic of a clamped cell being screened with various compounds.

FIG. 5 sets forth an exemplary embodiment of practicing the subject invention. In a first step 100, the pipette 16 is provided, and, then mounted in an electrode holder. Slight positive pressure is generated within the pipette (step 102) and current clamp mode is activated in the recording electrode 28 to monitor the pipette voltage (step 104). The pipette 16 is then submerged towards the liquid suspension 10 in step 106 with slight or no positive pressure being generated in the pipette 16 and ejected from the aperture 26. In this manner, objects (e.g., cell debris; dead cells) in the liquid suspension 10, including the cells 14, are urged away from the tip 24. Pipette voltage is monitored to determine when the pipette finds (i.e., engages) the liquid suspension (box 108).

Once the pipette has found the liquid suspension, and is partially submerged therein, the pipette is caused to slowly further submerge into the liquid suspension and approach the interface (step 110). In step 112, using any of the aforementioned techniques, the tip 24 of the pipette 16 is positioned in, or in proximity to, the interface 12 (as described above). Once properly positioned, the recording electrode 28 is switched to voltage clamp mode to monitor pipette resistance (step 114). Thereafter, as indicated in step 116, any positive pressure in the pipette 16 is replaced with negative pressure, such that a slight suction effect is generated through the aperture 26. At this point, it is desired to have the tip 24 contact one of the cells 14. One of the cells 14 may randomly contact the tip 24 and become sealed thereto. The contacting of the cell 14, and seal formation, are monitored by changes in electrical resistance in the pipette 16 measured by the recording electrode 28. As an alternative, an electrical field may be generated at the tip 26 to draw one of the cells 14 thereto, in a technique known to those skilled in the art as "electrofocusing". Seal formation is monitored using resistance of the recording electrode 28 (step 118), and, if seal formation does not occur (box 120), a holding potential (~−60 mV) is added to the pipette 16 (step 122). If seal formation still does not occur, additional negative pressure is applied (step 116).

Techniques for achieving cell contacting and seal formation are known in the prior art, and any such technique may be used in conjunction with the subject invention.

With seal formation, on cell or whole cell access may be achieved with the cell 14 and electrophysiological characteristics may be tested using known techniques.

Figure 6:
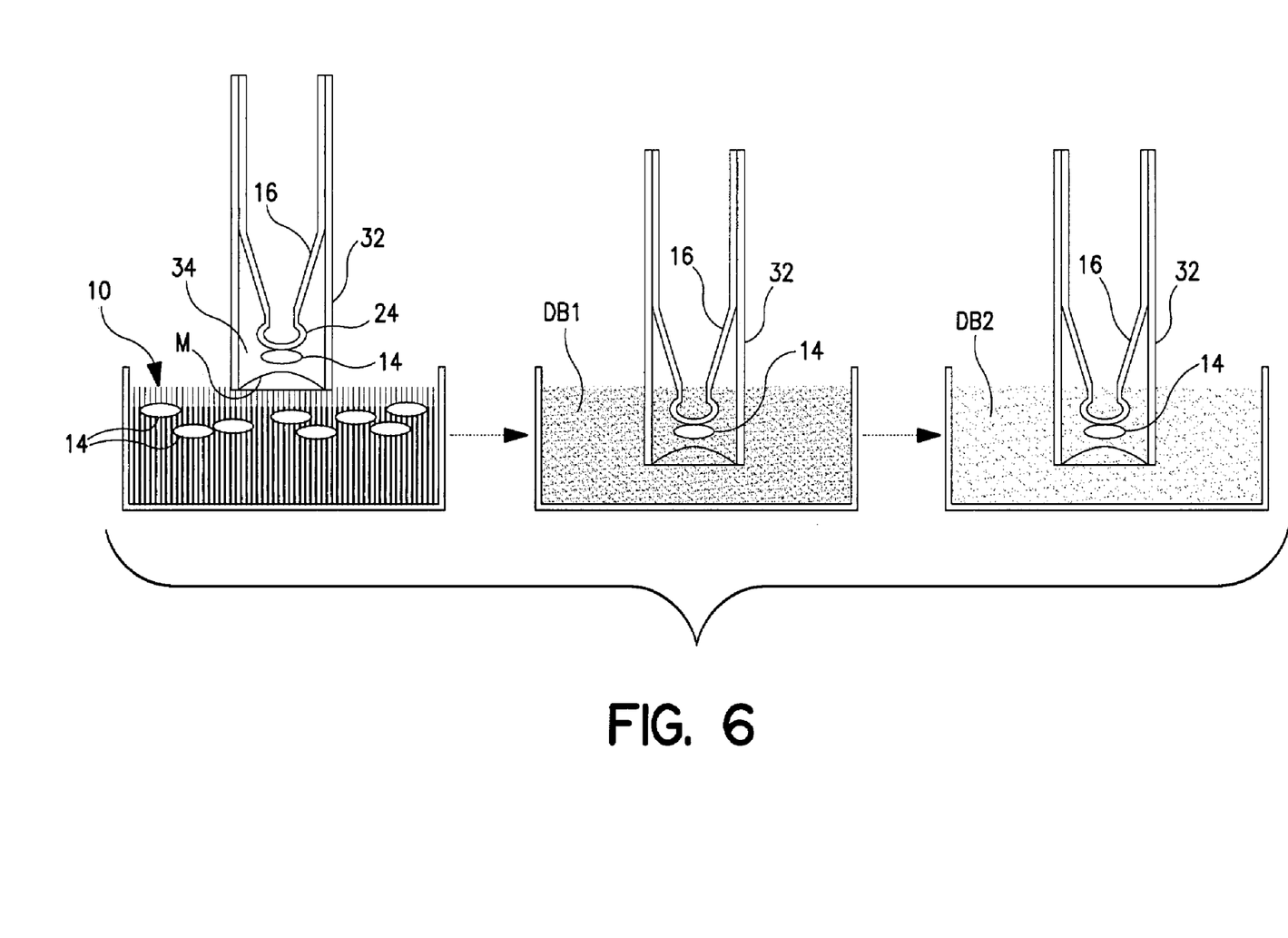

The liquid suspension 10 may be simultaneously prepared in multiple wells of a multiwell plate to allow for high-throughput screening (HTS) useable with bioassays. Because of the conduciveness of the invention to be used with automation, multiple cells can be simultaneously clamped to an array of pipettes 16 (corresponding to the wells of the multiwell plate) and then moved to cell baths for screening compounds. Effects of exposure of the compound(s) on the clamped cell(s) can be evaluated in view of electrophysiological activity of the cell ion channels, electrogenic transporters, or other activities that affect the electrical properties of cells. Advantageously, the technique can be used for assaying and screening compounds to determine the effect of the compounds on the human ether a-go-go (HERG) gene product. The clamped cells may be introduced to various compounds in a single bath, and/or sequentially introduced to various baths of one or more compounds, with cell washes being provided as needed. In this manner, the inventive technique decreases the time (and costs) of conducting the assays due, at least in part, to the speed and accuracy with which patch clamping can be achieved. For example, with reference to FIG. 6, the clamped cell 14 may be moved from drug bath DB1 to drug bath DB2. Preferably, to enhance seal integrity, the guard pipette 32 may be utilized so as to cover the tip 24 and the clamped cell 14. A volume of liquid 34 (such as saline) may be disposed within the guard pipette 32. The sealed cell 14 is preferably wholly submerged within the volume of liquid 34 so as to maintain the integrity of the seal. A meniscus M extends across the guard pipette 32. The volume of liquid 34 is maintained within a reservoir formed at the end of the guard pipette 32/pipette 16 assembly by surface tension extending across the guard pipette 32 and capillary attraction of the volume of liquid to the walls of the reservoir. The volume of liquid 34 maintains the electrical and mechanical stability of the seal of the cell 14 by ensuring that the cell 14 does not encounter an air/liquid interface during the course of an experiment.

The techniques described herein may be applied to other cell membrane receptors (e.g., guanine protein-coupled receptors (GPCR's)) and to other cell membrane-dependent phenomena, such as secretion and receptor cycling.

While the invention has been described in relation to the preferred embodiments with several examples, it will be understood by those skilled in the art that various changes may be made without deviating from the spirit and scope of the invention as defined in the appended claims.

What is claimed is:

1. A method for performing patch-clamp testing of electrical characteristics of cells, said method comprising the steps of:
   suspending a plurality of cells in a liquid suspension of at least first and second liquid layers, said first and second liquid layers having distinct densities so as to define an interface therebetween;
   inserting a micropipette into said liquid suspension; and,
   positioning a tip of said micropipette in or proximal to said interface such that said tip is positioned to contact one of said cells.

2. A method as in claim 1, further comprising the step of facilitating the attachment of one of said cells to said tip of said micropipette.

3. A method as in claim 2, wherein the step of facilitating includes introducing negative pressure in said micropipette.

4. A method as in claim 2, wherein the step of facilitating includes creating an electrical field across said tip.

5. A method as in claim 1, wherein the step of positioning includes disposing a reference electrode in said liquid suspension and monitoring electrical potential difference between said micropipette and said reference electrode.

6. A method as in claim 5, wherein said reference electrode extends through said interface.

7. A method as in claim 1, wherein at least one of said layers includes varying densities.

8. A method as in claim 7, wherein said varying densities are gradiently disposed.

9. A method as in claim 1, wherein said first liquid layer is formed by a first liquid in a vessel, said first liquid having a first density, and disposing a second liquid atop said first liquid, said second liquid having a second density lower than said first density, wherein said first liquid defines said first liquid layer, and said second liquid defines said second liquid layer.

10. A method as in claim 9, further comprising the step of mixing said cells in said first liquid prior to the step of disposing said second liquid.

11. A method as in claim 1, wherein said liquid suspension is contained within a well of a multiwell plate.

12. A method as in claim 1, wherein said first liquid layer includes a density modifying agent.

13. A method as in claim 1, wherein said second liquid layer is an extracellular saline solution.

14. A method as in claim 1, wherein the density of said cells is less than the density of said first layer.

15. A method as in claim 14, wherein the density of said cells is greater than the density of said second layer.

16. An assay for determining electrophysiological activity of cells including cellular resistance, capacitance, transmembrane potential, and conductance in response to various compounds, said assay comprising:
   suspending a plurality of cells in a liquid suspension of at least first and second liquid layers, said first and second liquid layers having different densities so as to define an interface therebetween;
   obtaining an electrically-acceptable seal between one of said suspended cells and a tip of a micropipette; and,
   introducing said sealed cell to one or more compounds to evaluate electrophysiological activity of the sealed cell in response thereto.

17. A method for screening compounds which affect electrophysiological characteristics of cells including cellular resistance, capacitance, transmembrane potential, and conductance, said method comprising:
   suspending a plurality of cells in a liquid suspension of at least first and second liquid layers, said first and second liquid layers having different densities so as to define an interface therebetween;
   obtaining an electrically-acceptable seal between one of said cells and a tip of a micropipette;
   introducing said sealed cell to one or more compounds; and
   evaluating electrophysiological characteristics of said sealed cell in response to said one or more compounds.

18. A method for screening compounds which effect a human ether-a-go-go (HERG) gene product, said method comprising:
   suspending a plurality of cells in a liquid suspension of at least first and second liquid layers, said first and second liquid layers having different densities so as to define an interface therebetween;
   obtaining an electrically-acceptable seal between one of said cells and a tip of a micropipette;
   introducing said sealed cell to one or more compounds; and
   determining the effect of said compounds on the HERG gene product of said sealed cell.

19. A method of preparing for an assay for determining electrophysiological activity of cells in response to various compounds, said method comprising:
   suspending a plurality of cells in a liquid suspension of at least first and second liquid layers, said first and second liquid layers having different densities so as to define an interface therebetween; and
   obtaining an electrically-acceptable seal between one of said suspended cells and a tip of a micropipette.

20. A method of preparing for an assay for determining the effect of various compounds on a human ether a-go-go (HERG) gene product, said method comprising:
   suspending a plurality of cells in a liquid suspension of at least first and second liquid layers, said first and second liquid layers having different densities so as to define an interface therebetween; and
   obtaining an electrically-acceptable seal between one of said suspended cells and a tip of a micropipette.

* * * * *